United States Patent
Moskal

(10) Patent No.: US 9,804,274 B2
(45) Date of Patent: Oct. 31, 2017

(54) HYBRID TOF-PET/CT TOMOGRAPH COMPRISING POLYMER STRIPS MADE OF SCINTILLATOR MATERIAL

(71) Applicant: UNIWERSYTET JAGIELLONSKI, Cracow (PL)

(72) Inventor: Pawel Moskal, Czulowek (PL)

(73) Assignee: UNIWERSYTET JAGIELLONSKI, Cracow (PL)

( * ) Notice: Subject to any disclaimer, the term of this patent is extended or adjusted under 35 U.S.C. 154(b) by 102 days.

(21) Appl. No.: 14/915,255

(22) PCT Filed: Aug. 29, 2014

(86) PCT No.: PCT/EP2014/068363
§ 371 (c)(1),
(2) Date: Feb. 29, 2016

(87) PCT Pub. No.: WO2015/028598
PCT Pub. Date: Mar. 5, 2015

(65) Prior Publication Data
US 2016/0209514 A1    Jul. 21, 2016

(30) Foreign Application Priority Data

Aug. 30, 2013 (PL) .................................. P.405181

(51) Int. Cl.
*A61B 6/00* (2006.01)
*G01T 1/16* (2006.01)
*G01T 1/29* (2006.01)
*A61B 6/03* (2006.01)

(52) U.S. Cl.
CPC ............ *G01T 1/1603* (2013.01); *A61B 6/032* (2013.01); *A61B 6/037* (2013.01); *G01T 1/2985* (2013.01)

(58) Field of Classification Search
CPC ........ G01T 1/1603; A61B 6/037; A61B 6/032
USPC .......... 378/19, 62, 98.8; 250/370.08, 370.09, 250/370.11
See application file for complete search history.

(56) References Cited

U.S. PATENT DOCUMENTS 6,448,559 B1 *   9/2002   Saoudi ................. G01T 1/1603
                                                          250/367
7,939,808 B1 *   5/2011   Shah ...................... G01T 1/202
                                                          250/370.11

\* cited by examiner

*Primary Examiner* — Courtney Thomas
(74) *Attorney, Agent, or Firm* — Mark M. Friedman

(57) ABSTRACT

A hybrid TOF-PET/CT tomograph comprising a detection chamber, gamma radiation detectors, X-ray detectors and a movable X-ray source, wherein the gamma radiation detectors (150, 250, 350, 450, 550) and the X-ray detectors (170, 270, 370, 470, 570) surround the detection chamber (102, 202, 302, 402, 502) around the whole perimeter of the detection chamber (102, 202, 302, 402, 502), and wherein the gamma radiation detectors (150, 250, 350, 450, 550) are located closer to the longitudinal axis (115, 215, 315, 415, 515) of the detection chamber (102, 202, 302, 402, 502) than the X-ray detectors (170, 270, 370, 470, 570), and wherein the gamma radiation detectors (150, 250, 350, 450, 550) comprise polymer strips (151, 251, 351, 451, 551) made of a scintillation material having a density lower than the density of the X-ray radiation detectors (171, 271, 371, 471, 571).

19 Claims, 4 Drawing Sheets

HYBRID TOF-PET/CT TOMOGRAPH COMPRISING POLYMER STRIPS MADE OF SCINTILLATOR MATERIAL

TECHNICAL FIELD

The present disclosure relates to a hybrid TOF-PET/CT tomograph, comprising a TOF-PET tomograph and a CT tomograph.

BACKGROUND

Images of the interiors of bodies may be acquired using various types of tomographic techniques, which involve recording and measuring radiation from tissues and processing acquired data into images.

One of these tomographic techniques is positron emission tomography (PET), which involves determining spatial distribution of a selected substance throughout the body and facilitates detection of changes in the concentration of that substance over time, thus allowing to determine the metabolic rates in tissue cells.

The selected substance is a radiopharmaceutical administered to the examined object (e.g. a patient) before the PET scan. The radiopharmaceutical, also referred to as an isotopic tracer, is a chemical substance having at least one atom replaced by a radioactive isotope, e.g. $^{11}C$, $^{15}O$, $^{13}N$, $^{18}F$, selected so that it undergoes radioactive decay including the emission of a positron (antielectron). The positron is emitted from the atom nucleus and penetrates into the object's tissue, where it is annihilated in reaction with an electron present within the object's body.

The phenomenon of positron and electron annihilation, constituting the principle of PET imaging, consists in converting the masses of both particles into energy emitted as annihilation photons, each having the energy of 511 keV. A single annihilation event usually leads to formation of two photons that diverge in opposite directions at the angle of 180° in accordance with the law of conservation of the momentum within the electron-positron pair's rest frame, with the straight line of photon emission being referred to as the line of response (LOR). The stream of photons generated in the above process is referred to as gamma radiation and each photon is referred to as gamma quantum to highlight the nuclear origin of this radiation. The gamma quanta are capable of penetrating matter, including tissues of living organisms, facilitating their detection at certain distance from object's body. The process of annihilation of the positron-electron pair usually occurs at a distance of several millimetres from the place of the radioactive decay of the isotopic tracer. This distance constitutes a natural limitation of the spatial resolution of PET images to a few millimetres.

A PET scanner comprises detection devices used to detect gamma radiation as well as electronic hardware and software allowing to determine the position of the positron-electron pair annihilation event on the basis of the position and time of detection of a particular pair of the gamma quanta. The radiation detectors are usually arranged in layers forming a ring around object's body and are mainly made of an inorganic scintillation material. A gamma quantum enters the scintillator, which absorbs its energy to re-emit it in the form of light (a stream of photons). The mechanism of gamma quantum energy absorption within the scintillator may be of dual nature, occurring either by means of the Compton's effect or by means of the photoelectric phenomenon, with only the photoelectric phenomenon being taken into account in calculations carried out by current PET scanners. Thus, it is assumed that the number of photons generated in the scintillator material is proportional to the energy of gamma quanta deposited within the scintillator.

When two annihilation gamma quanta are detected by a pair of detectors at a time interval not larger than several nanoseconds, i.e. in coincidence, the position of annihilation position along the line of response may be determined, i.e. along the line connecting the detector centres or the positions within the scintillator strips where the energy of the gamma quanta was deposited. The coordinates of annihilation place are obtained from the difference in times of arrival of two gamma quanta to the detectors located at both ends of the LOR. In the prior art literature, this technique is referred to as the time of flight (TOF) technique, and the PET scanners utilizing time measurements are referred to as TOF-PET scanners. This technique requires that the scintillator has time resolution of a few hundred picoseconds.

CT (Computed Tomography) is one of the transmission methods used for imaging. This technique involves a measurement of X-ray radiation that penetrates through the object's body. Examination with the use of computer tomography involves multiple irradiation of the object with a suitably formed, i.e. collimated x-ray beam, and CT detectors measure the final intensity of the radiation beam, which, after penetration through the object's body, is weakened to various degrees—depending on the type of tissue through which radiation penetrates. The obtained signals provide the object's anatomical image on the basis of information concerning the distribution of electron density in tissues.

Superimposing of a functional image (PET) over an anatomical image (CT) considerably increases the capabilities of imaging techniques: a PET image enables precise positioning of metabolic changes in individual organs and the determination of the degree of these changes, whereas the obtainment of a CT image at the same time allows a precise allocation of these changes to respective organs. Obtained hybrid PET/CT images may be useful in scientific research on physiological processes and in testing the action of new medicines, where it is especially important to precisely assign to respective tissues metabolic changes of tested radiopharmaceuticals, during imaging.

In currently used PET/CT tomographs, the PET detector ring is spatially separated from the CT detector ring by ca. 60 cm. Therefore, imaging: PET and CT are actually carried out at various positions of the examined object and at different times. During the first examination stage, a CT scan is done in such a way that the object is continuously shifted along the tomograph, and then a PET tomograph examination is carried out, in which, in order to generate an image larger that the width of the PET tomograph detection ring, the object is shifted between individual imaging events in increments, ca. at ⅔ of the tomograph detection field width. Therefore, body imaging within an area larger than the longitudinal PET field of view requires that the object should be put in motion and stopped between individual imaging events. This procedure involves a threat that image distortions, so-called artefacts, may occur, especially in abdominal cavity organs, which may move between individual scanning events due to accelerations to which the object is subjected during shifting. Moreover, the superimposing of PET and CT images, taken in different times, requires that additional corrections should be introduced due to the weakening activity of the radiopharmaceutical and metabolic processes; what also needs to be remembered is that each of these corrections is additionally exposed to systemic errors that occur when the images are superimposed.

Patent literature lists solution methods with respect to the described difficulties, and tomographs enabling PET and CT scanning.

An American patent description, U.S. Pat. No. 7,170,971, presents a tomograph in which scanning with CT and SPECT detectors can be done at the same time (i.e. detectors used in single photon emission computed tomography). Detectors are placed on the tomograph arm that has two angular degrees of freedom, and additionally, also three translation degrees of freedom, within a specific range. The solution allows a sequential imaging, applying various methods. Also, imaging with the use of two different methods is possible at the same time; what must be borne in mind is that due to a small solid angle that can be covered by detectors in the described configuration, this method does not enable a simultaneous imaging of the entire body or larger body parts. The described device is optimised so that it can carry out imaging of individual organs, such as the heart, while the CT tomograph used in this solution is a second-generation tomograph combined with a conical x-ray radiation beam. Such a solution would be impractical in hybrid PET/CT tomographs.

A solution is known from an American patent application US20020090050, which enables the use of the same detectors to carry out PET and CT tomography within a specific area on the object's body, which allows a reduction of size and mass of the tomograph arm. Electronic circuits are connected to PET and CT detectors, processing discrete signals as well as integrating systems. PET and CT imaging is done sequentially: the tomograph arm rotates and a CT image is collected; then, the detector configuration is changed, the tomograph arm rotates and a PET image is collected. During scanning, the object is shifted against the detectors. The tomograph works in three data collection modes: discrete for PET, and integrating for CT, and it can collect discrete signals during CT acquisition. The configuration of detectors in the presented solution does not, however, permit the scanning of a full perimeter around the object. Moreover, the detector configuration must be changed in such a manner that in one setting, two detector blocks are shifted to one side for CT imaging, whereas in the other, detector blocks are positioned opposite each other, for PET imaging. On the basis of the presented solution, a lo detector can be built, which would cover the entire perimeter around the object, with a tube generating x-ray radiation, rotating outside the detectors' axis. However, the solution with the tube rotating outside the detector will not allow the obtainment of good CT image resolutions in a full object's volume, as far as a tomograph with a large longitudinal field of view is concerned.

In article "A Modular VME Or IBM PC Based Data Acquisition System For Multi-Modality PET/CT Scanners Of Different Sizes And Detector Types" (D. B. Crosetto et al., The Internet Journal of Medical Technology 2003 Vol. 1. No. 1), a device was described, which enabled simultaneous PET and CT imaging of the entire object's body. This solution contained detectors presented in US20020090050 patent application. The solution eliminates the formation of potential artefacts caused by the object movement between subsequent imaging sessions. According to the solution presented, each detection module is built of three types of crystals: CsI(TI), LSO, GSO. Out of the discussed crystals, LSO has the best time properties, enabling the use of information concerning differences during the registration of annihilation quanta: TOF-PET. However, the signal decay time, even for LSO crystal, being 40 ns (nanoseconds), is such large that allow data collection in CT tomography, in a signal counting mode at a maximum of $10^7$ signals per converter. Moreover, the operation of signals in an integration mode, as described in the CT detector solution, is distorted by fluorescent effects.

Currently, intensive research is carried out concerning the design of such CT and PET detectors that would successfully satisfy stringent requirements with respect to PET and CT tomographs. In a doctoral thesis, entitled: "Combined detector in positron and x-ray tomography" (A. T. Nassalski, The Andrzej Sołtan Institute for Nuclear Studies, Świerk 2010), results of research on PET and CT tomographs are presented.

The currently used PET technology is costly, mostly due to the prices of scintillators and electronics; also, it must be remembered that the cost of a conventional PET detector and electronics increases in proportion with the length of the longitudinal field of view in PET detectors. Therefore, one of the factors limiting mass production of hybrid PET/CT tomographs is high production cost of the PET tomographs with a large longitudinal field of view.

Patent application WO2011008119 describes an invention concerning the strip device and the method used in the determination of position and time of gamma quanta reaction, and the application of this device in PET tomography. The TOF-PET tomograph, described in the application, allows simultaneous imaging of whole object, while the material used to register gamma quanta is polymers doped with elements of high atomic numbers. The device described in this application reduces PET costs; however, the application does not describe a method of simultaneous PET & CT imaging with the use of polymer strip scintillators.

A Japanese patent application JP2004350942 discloses a tomographic device and a radiographic testing device simplifying a procedure in simultaneous imaging of a plurality of modalities and advancing the correction processing. An X-ray which is emitted from a circumferentially moving X-ray source and transmitted through a subject is detected using multiple radiation detectors disposed annularly and a plurality of pairs of gamma-ray emitted from the subject are detected. A computer selects an interest area inside the subject from an X-ray CT image and performs an image processing of function information on the subject using sectional or volume information on the selected interest area. The PET and CT detectors are arranged in a single detection layer. The detectors are made of an inorganic material (CdTe) and have a cubical shape.

It would be expedient to provide an imaging device with the use of economical polymer scintillators, which would enable simultaneous registration of gamma quanta and x-ray radiation quanta with a broad field of view, enabling the elimination of artefacts that could distort the image due to the movement of the object, and systematic errors formed during superimposure of images made at various positions and times. This will allow effective, simultaneous functional and anatomical imaging.

SUMMARY

There is presented a hybrid TOF-PET/CT tomograph comprising a detection chamber, gamma radiation detectors, X-ray detectors and a movable X-ray source, wherein the gamma radiation detectors and the X-ray detectors surround the detection chamber around the whole perimeter of the detection chamber, and wherein the gamma radiation detectors are located closer to the longitudinal axis of the detection chamber than the X-ray detectors, and wherein the gamma radiation detectors comprise polymer strips made of a scintillation material having a density lower than the density of the X-ray radiation detectors.

Preferably, the scintillation material of the polymer scintillation strips has a density below 1.2 g/cm$^3$.

Preferably, the X-ray detectors have a density over 6 g/cm$^3$.

Preferably, the polymer scintillation strips are penetrable for at least 60% of the X-rays.

Preferably, the scintillation strips are arranged circumferentially such that the longest edges of the strips are parallel to the longitudinal axis of the hybrid tomograph.

Preferably, the scintillation strips are adjacent to each other.

Preferably, the scintillation strips are spaced with respect to their longest edges.

Preferably, the X-ray detectors form a ring which is coaxial with the longitudinal axis of the hybrid tomograph and covering a TOF-PET detection layer.

Preferably, the layer of X-ray detectors has a cross-section, perpendicular to the longitudinal axis of the hybrid tomograph, in a form of an arc.

Preferably, an X-ray source is positioned between the layer of the gamma radiation detectors and the layer of X-ray detectors.

Preferably, the X-ray source is positioned on the outside of the gamma ray detectors layer.

Preferably, the X-ray source, during X-ray emission, simultaneously rotates around and moves along the longitudinal axis of the hybrid tomograph.

Preferably, the X-ray detectors change their position relative to the gamma radiation detectors.

Preferably, the collimated X-ray beam does not pass through any scintillation strip.

Preferably, the collimated X-ray beam passes through two scintillation strips.

Preferably, electronic devices connected to the PET tomograph detectors and to the CT tomograph detectors, as well as the PET photomultipliers are located outside the detection chamber.

Preferably, the gamma radiation detectors and the X-ray detectors are connected to a common clock signal.

Preferably, the tomograph is configured for simultaneous TOF-PET and CT imaging.

Preferably, the tomograph is configured for sequential TOF-PET and CT imaging.

BRIEF DESCRIPTION OF FIGURES

Example embodiments are presented on a drawing wherein.

DETAILED DESCRIPTION

Specific indications in the figures mean respectively:
101, 201, 301, 401, 501—hybrid TOF-PET/CT tomograph; 102, 202, 302, 402, 502—detection chamber; 103, 203, 303, 403, 503—platform; 104, 204, 304, 404, 504—imaged object (patient); 150, 250, 350, 450, 550—layer of detectors registering gamma radiation; 151, 251, 351, 451, 551—low density polymer scintillator strip registering gamma quanta; 160, 260, 360—tube emitting X-rays; 161, 261, 361—arrows indicating components of direction of movement of the tube which emits X-rays; 170, 270, 370, 470, 570—layer of detectors registering X-rays; 171, 271, 371, 471, 571—high density scintillation crystals registering X-rays; 372—direction of movement of gamma radiation detection layer; 108, 408, 508—collimated X-ray beam in a fan form, in a plane perpendicular to the longitudinal axis of the tomograph; 208, 308—collimated X-ray beam in a fan form, in a plane comprising longitudinal axis of the tomograph; 462, 562—rotating electron beam; 460, 560—target of rotating electron beam; 461, 561—movement direction arrows for rotating electron beam; 115, 215, 315, 415, 515—longitudinal axis of the detection chamber.

Figure 1:
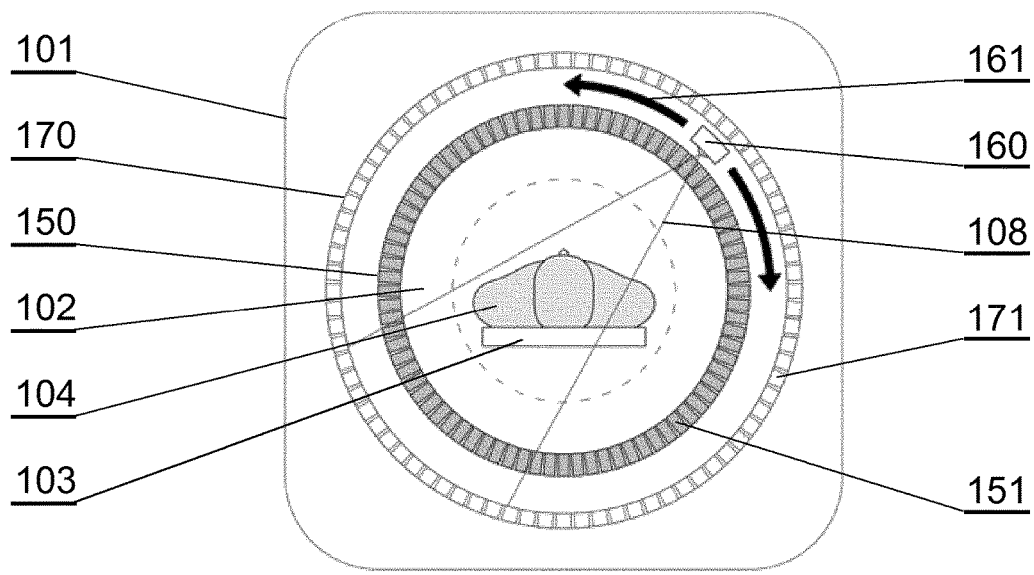
FIG. 1 presents a diagram of TOF-PET/CT hybrid tomograph in the first exemplary embodiment, in a cross-section; the x-ray beam in the form of a fan, in a plane perpendicular to the tomograph longitudinal axis.
Figure 2:
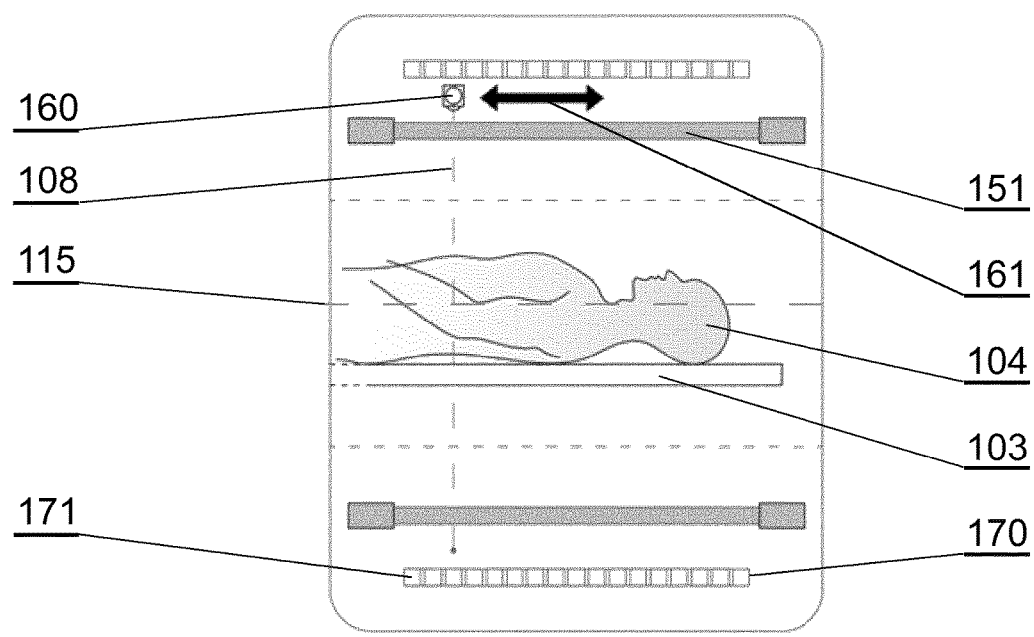
FIG. 2 presents a diagram of TOF-PET/CT hybrid tomograph in the first exemplary embodiment, in a longitudinal section; the x-ray beam in the form of a fan, in a plane perpendicular to the tomograph longitudinal axis.

FIGS. 1-2 show an overview of a hybrid TOF-PET/CT tomograph 101 in the first embodiment. The hybrid tomograph 101 comprises a detection chamber 102, a platform 103, an inner layer of detectors 150 registering gamma radiation, comprising polymer scintillators 151 of low density, a moving source of X-ray 160 and an outer layer of detectors 170 registering X-rays, and comprising scintillation crystals 171 of high density.

In the first stage, an object 104—upon administration of a radiopharmaceutical—is introduced into the chamber 102 via the platform 103, which remains stationary during the second stage—scanning of the object 104. During a scan of the object 104, gamma quanta produced by decay of the radioactive tracer are recorded by the inner layer of gamma detectors 150, which may be made of thin polymer scintillator 151 strips of low density, for example, of size: 5 mm wide, 20 mm thick, and of length depending on the desired longitudinal field of view of the hybrid tomograph 101. Strips 151 may be arranged circumferentially in hybrid tomograph 101—forming an inner layer of gamma radiation detectors immediately surrounding the object 104, or may be covered by the housing, preferably made of plastic material—having an aesthetic function, wherein the housing material should be selected to pass gamma radiation and X-rays. Strips 151 in layer 150 can be spaced apart at predetermined distance or may adjoin each other along their longest edges to form an elongated, cylindrical ring (or another shape) coaxial with the longitudinal axis 115 of the hybrid tomograph 101.

At the time of PET scanning, CT scanning may also be carried out. FIG. 1-6, with black arrows 161, 261, 361 indicate two components of direction of movement of an X-ray tube 160, 260, 360, which rotates around the object 104, 204, 304 and around the inner layer of gamma radiation detectors 150, 250, 350 along a helical path (same as in the case of conventional fourth generation CT tomographs), wherein the path of movement of the tube 160, 260, 360 may extend through the entire length of the hybrid tomograph 101, 201, 301, whereas the length of the hybrid tomograph 101, 201, 301 may preferably be from a few centimetres to several meters. The tube 160, 260, 360 can emit a beam of X-rays in the form of a fan, for example, by means of collimators (not shown), wherein FIGS. 1-2 depict schematically a collimated beam of X-rays 108 in the form of a fan and located in a plane extending perpendicular to the longitudinal axis 115 of the tomograph. The tube, from the outer side, may be surrounded by a layer of X-ray detectors 170.

Figure 3:
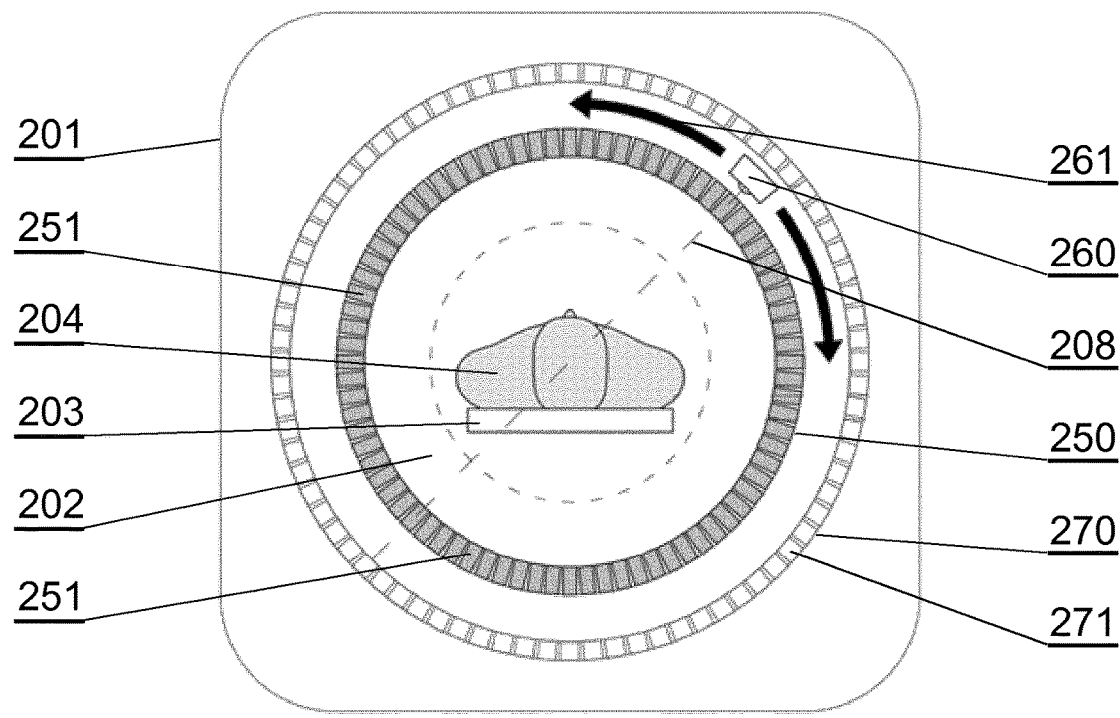
FIG. 3 presents a diagram of TOF-PET/CT hybrid tomograph in the second exemplary embodiment, in a cross-section; the x-ray beam in the form of a fan, in a plane containing the tomograph longitudinal axis.
Figure 4:
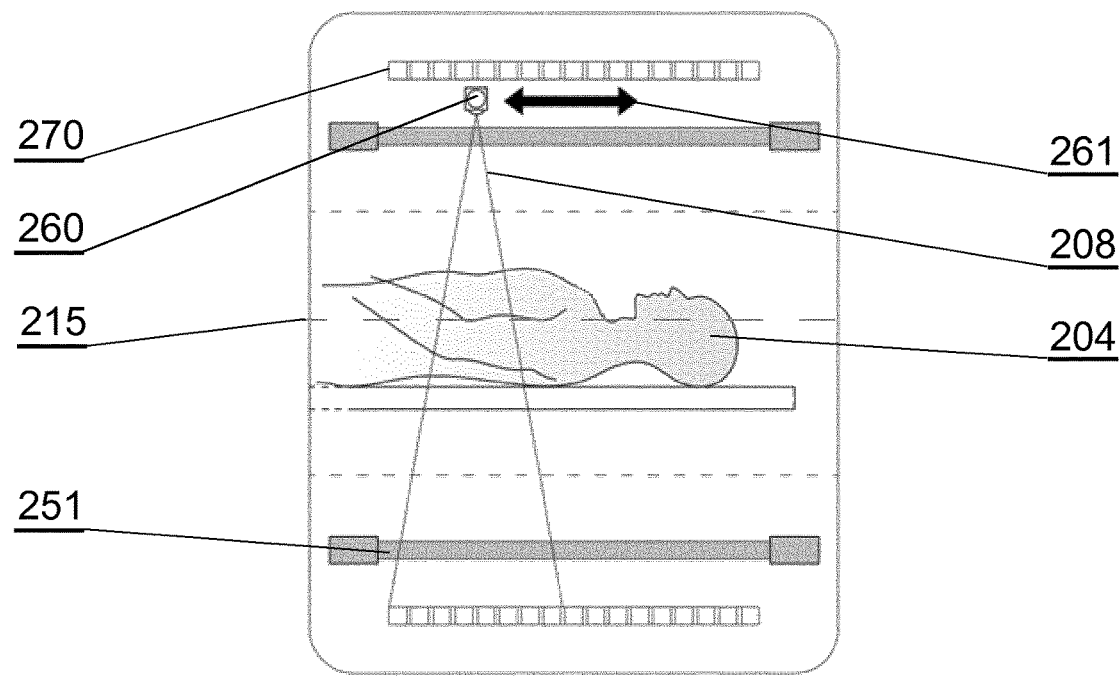
FIG. 4 presents a diagram of TOF-PET/CT hybrid tomograph in the second exemplary embodiment, in a longitudinal section; the x-ray beam in the form of a fan, in a plane containing the tomograph longitudinal axis.

FIG. 3-4 illustrate schematically a hybrid TOF-PET/CT tomograph 201 in the second embodiment with the collimated beam of X-rays 208 formed into a fan, and extending in a plane parallel to the longitudinal axis of the tomograph. The trajectory of movement of the tube 260 can be surrounded from the outside by a ring of the CT detectors 271, forming the outer detection layer 270, wherein the X-ray detectors 271 may form a cylindrical ring around the object extending coaxially with the longitudinal axis 201 of the hybrid tomograph at any length, depending on the desired longitudinal field of view of the tomograph 201. Each detector 271 may be made of inorganic scintillation crystals, semi-conductive scintillators, or any other conventional scintillators capable of registering X-rays. Tube 260 moving around the object 204 emits X-ray beam in the direction of longitudinal axis of the tomograph, part of which penetrates the body and is detected by opposed detectors 270, which allows obtaining a CT image of the whole body without the necessity of moving the object 204 during scanning.

Imaging using PET detectors (gamma radiation detectors), and CT detectors (X-ray detectors) using a hybrid TOF-PET/CT tomograph 101, 201, 301, 401, 501 (FIG. 1-8) can be performed simultaneously or sequentially, wherein the sequential imaging can be made according to the desired sequence or, depending on the needs of imaging, it can also be performed only with PET detectors or using only CT detectors.

Data obtained from scanning of both scanners (TOF-PET and CT) can be saved along with the time stamp synchronized with respect to a common clock, which enables superimposition of PET and CT images performed at the same intervals. Data acquisition and subsequent PET and CT images reconstruction procedures are based on solutions known in the art.

In the solution according to the second embodiment (FIG. 3-4) it is possible to collimate an X-ray beam 208 so that the beam width does not exceed the width of a single detection strip 251 of the PET tomograph, which allows simultaneous TOF-PET and CT imaging for unlimitedly large X-ray beams and operation of the CT tomograph in the current integration mode. Taking into consideration the fact that the decay time of light signals in the polymer scintillators is less than 2 ns (nanoseconds), and that the probability of reaction of the X-ray quanta of known energy of about 100 keV in a polymer of thickness of 2 cm is about 0.2, TOF-PET detectors 250 operating in the signal counting mode offer the possibility to distinguish between a signal from X-ray radiation and a signal from annihilation quanta of the gamma radiation at a frequency of X-ray beam of even $10^8$ X-ray quanta per second.

Design of tomograph 201 allows simultaneous TOF-PET and CT imaging even for higher values of intensity of X-ray beam, wherein during the image reconstruction it is possible not to take into account the signal that originated in the scintillation strip 251 when the strip 251 was passed through by the X-ray beam.

Figure 5:
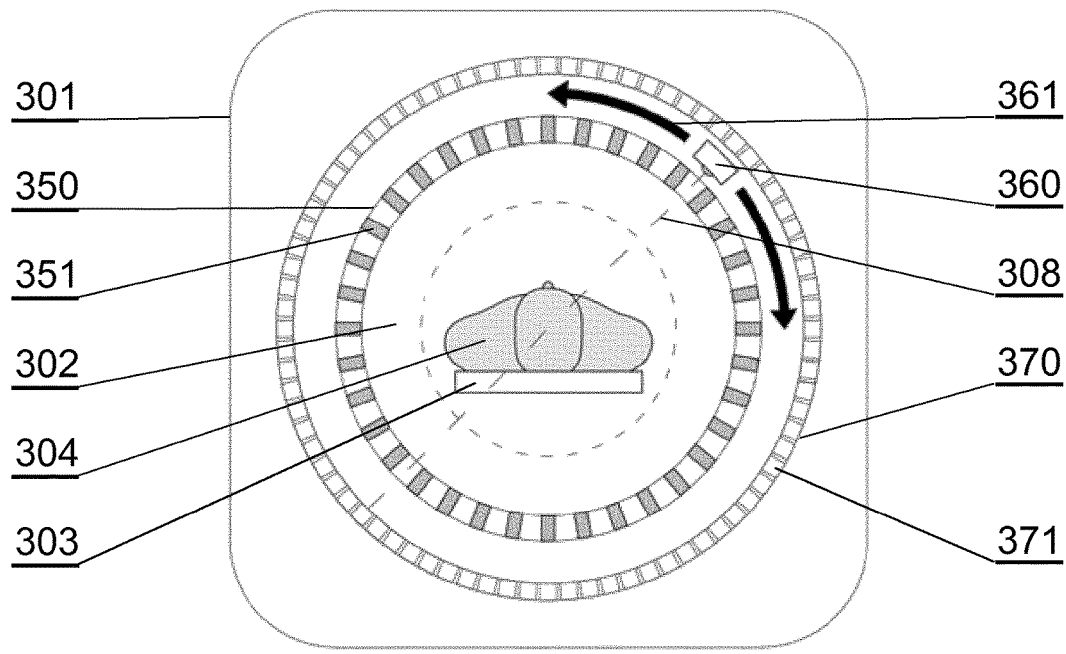
FIG. 5 presents a diagram of TOF-PET/CT hybrid tomograph in the third exemplary embodiment, in a cross-section, with gamma radiation detectors in an expanded arrangement.
Figure 6:
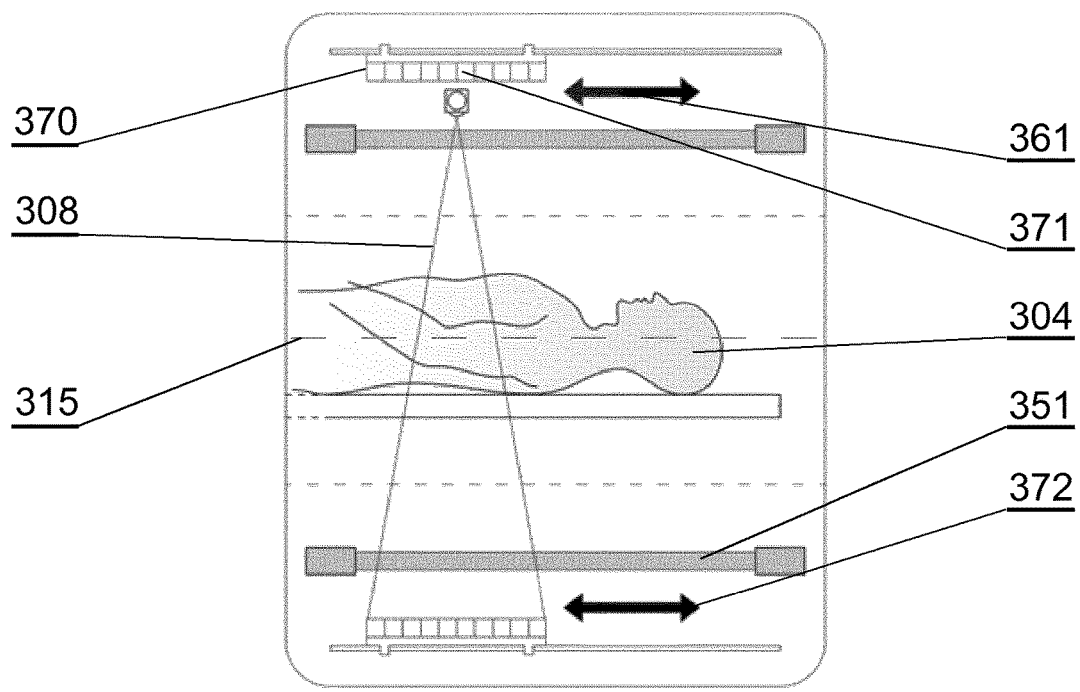
FIG. 6 presents a diagram of TOF-PET/CT hybrid tomograph in a version that can be used in combination with the first, second and third exemplary embodiment, in a cross-section, with a mobile layer of x-ray radiation detectors.

FIG. 5-6 shows schematically a hybrid TOF-PET/CT tomograph in the third embodiment. The tomograph 301 allows simultaneous TOF-PET and CT imaging without the X-ray beam attenuation in the polymer strips of PET detectors 351.

In order to perform CT scanning using X-ray beam of high intensity, for example greater than $10^8$ of X-ray quanta per second, it is possible to use gamma radiation detection layer 350 with scintillation strips spaced as shown in FIG. 6. For such a structure of a hybrid tomograph 301, the X-ray beam 308 emitted by rotating tube 360 may be registered by CT detectors 371 for the range of angles for which the beam 308 passes only through the object's body 304. For example, for a ring of a diameter of 100 cm formed by scintillation PET strips 351, each having a thickness of 5 mm and with a gap between adjacent strips of thickness of 3 mm, 392 CT projections can be obtained.

The design of the tomograph according to the third embodiment not only enables moving the lamp 360, but also layer of CT detectors 370, wherein the CT detectors 371 forming a ring around the object (FIG. 6) are movable in a plane parallel to the longitudinal axis of the hybrid tomograph 301, and the speed of the ring 370 can be chosen independently of the movement of the tube 360 or in such a way that at any time the range of the X-ray beam 308 will coincide with the CT detectors layer 370. The direction of movement of detectors 370 is schematically shown by arrow 372 in FIG. 6.

Solutions according to the first, second and third embodiment make it possible to produce a less expensive version of a hybrid TOF-PET/CT tomograph with a narrow ring of CT detectors 370 (FIG. 6). In the case of application of polymer strip scintillators as gamma radiation detectors 351 for which the cost of the detection material and electronics generally does not depend on the length of the field of view provided by the detectors 351, and using a CT tomograph with a narrow ring of detectors 370, one can get a relatively inexpensive hybrid tomograph with a wide field of view, compared to conventional TOF-PET/CT tomographs.

The hybrid tomograph 101, 201, 301 as presented herein, shown in the embodiments in FIG. 1-6, comprises a hollow space between the layer of gamma radiation detectors 150, 250, 350, and the layer of X-ray detectors 170, 270, 370; the hollow space can be used to install a structure to move the mechanism with a rotating tube 160, 260, 360. For example, such a structure may be based on a number of rigid rods arranged parallel to the main axis of the tomograph (not shown).

Figure 7:
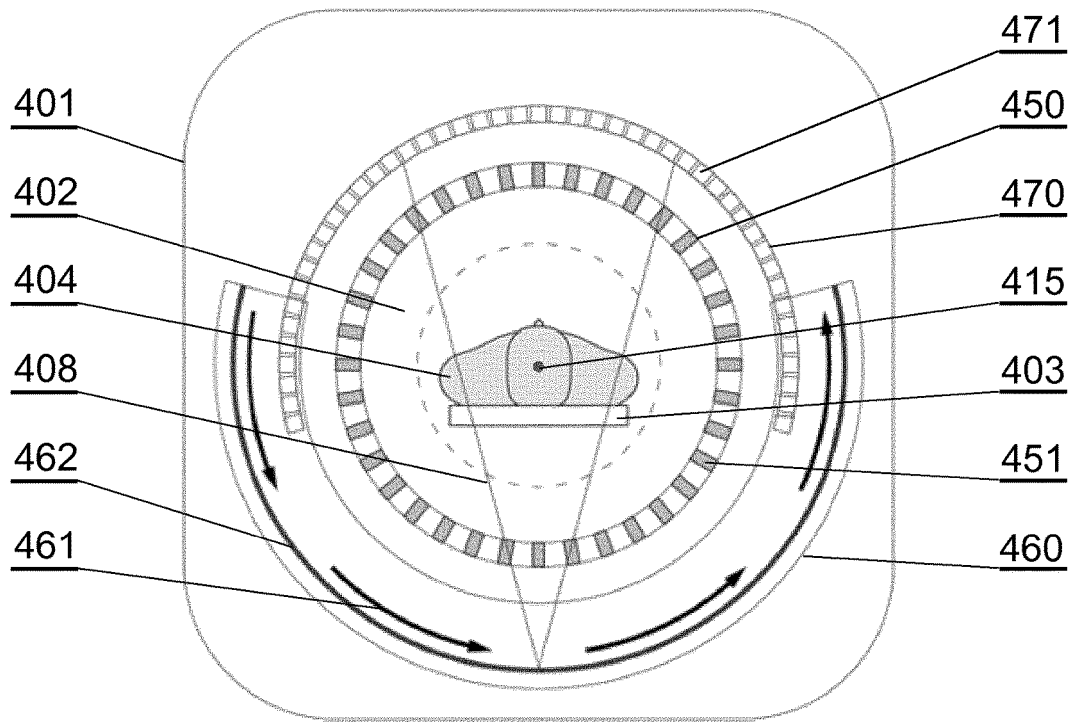
FIG. 7 presents a diagram of TOF-PET/CT hybrid tomograph in the fourth exemplary embodiment, in a cross-section, with x-ray beam generated as a result of a reaction of the rotating electron beam with a target; the tomograph having polymer strips spaced apart from each other.
Figure 8:
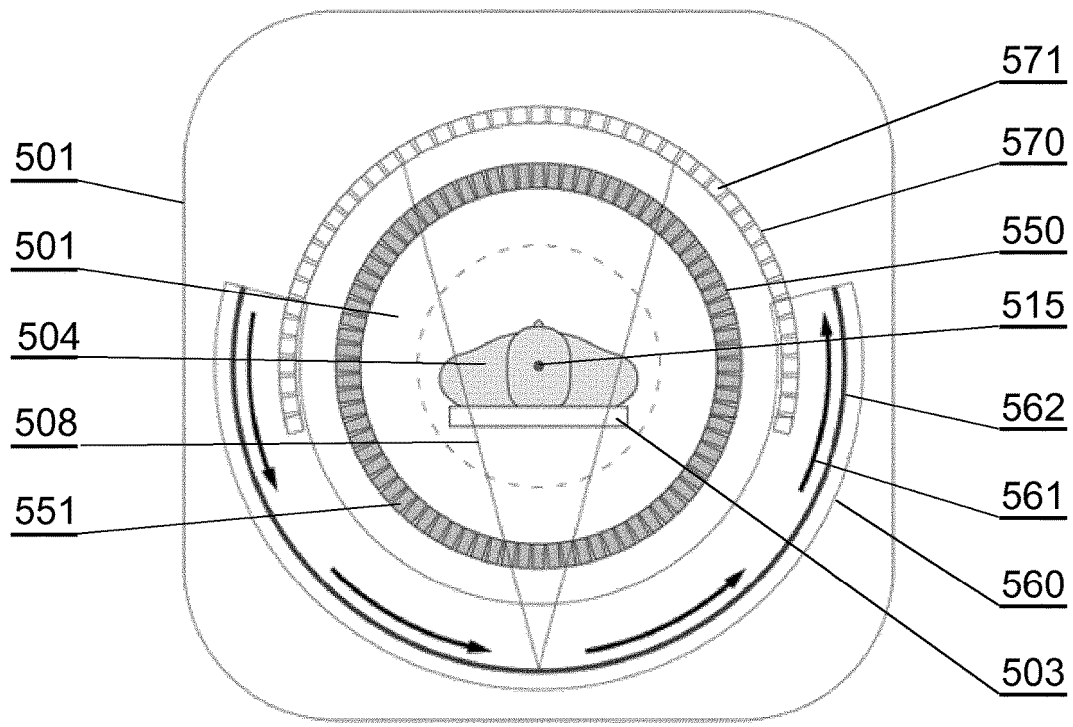
FIG. 8 presents a diagram of TOF-PET/CT hybrid tomograph in the fifth exemplary embodiment, in a cross-section, with x-ray beam generated as a result of a reaction of the rotating electron beam with a target; the tomograph having polymer strips adjoining each other.

FIG. 7 is a cross section of TOF-PET/CT hybrid tomograph 401 in the fourth embodiment, and FIG. 8 shows a PET/CT hybrid tomograph 501 in the fifth embodiment. In tomographs 401 and 501, to produce the x-ray beam, electron beam 462, 562 was used, which rotates along with the circle indicated by arrows 461, 561, wherein the electron beam 462, 562 by reaction with the target 460, 569 will produce X-ray beam 408, 508 which—after appropriate collimation—is used as X-ray source during a CT scan. Gamma radiation scintillation strips forming the inner detection layer 451 may be spaced apart as shown in FIG. 7. Gamma radiation scintillation strips forming the inner detection layer 551 may adjoin each other as shown in FIG. 8. The layer of X-ray detectors 470, 570 may form an arc.

Thanks to the use of X-ray scintillation detectors of a high density and gamma radiation polymer detectors of a low density, a device was constructed, in which, during scanning, neither PET and CT detection layers nor the object require movement. The PET detectors of a low density used in the device, forming the inner layer, may weaken the X-ray radiation beam arriving at CT detectors by not more than 40%, which is equivalent to absorption in about four-centimetre thick soft tissue layer, wherein the absorption can be accurately taken into account by earlier adjustment of TOF-PET/CT hybrid tomograph.

Generally, the density of the polymer strips of scintillation material should be lower than the density of scintillation material of X-ray radiation detectors, as it allows passing X-ray through PET detectors forming the inner detection layer, which may then be registered by the X-ray detectors forming the outer detection layer. It is preferred that the polymer scintillation strips have a density below 1.2 g/cm$^3$ as it allows penetration of X-rays in an amount necessary to obtain the CT projection. It is preferred that scintillation material of X-ray radiation detectors has a density above 6 g/cm$^3$ since it effectively absorbs X-rays. In particular, polymer scintillator strips can transmit at least 60% of X-rays, making it possible to build a layer of PET detectors surrounding the scintillation chamber around the entire circumference, and to locate X-ray detectors in the outer layer of the hybrid tomograph presented herein.

In addition, the hybrid tomograph presented herein can be designed in such a way that the PET photoelectric converters, combined with detectors and means for changing light impulses into electrical impulses, and all other electronics items designed to convert received signals into the image, can be located outside the field of view of the CT tomograph. Thanks to such a solution, even during simultaneous PET and CT imaging, electronics of PET detectors is not subjected to X-rays, which could distort the PET signals, and the beam emitted by the X-ray tube is not distorted by PET scanner electronics.

Thus, the resulting device enables detection of X-rays and gamma rays at the same time, wherein, depending on the length of the polymer scintillator strips, the device can be used to perform, at the same time, scanning of the whole body of an object without moving detectors, and without moving the object. This gives the possibility of producing hybrid TOF-PET/CT images free of any artefacts and systematic errors.

While the technical solutions presented herein have been depicted, described, and defined with reference to particular preferred embodiment(s), such references and examples of implementation in the foregoing specification do not imply any limitation on the invention. Various modifications and changes may be made thereto without departing from the scope of the technical solutions presented. The presented embodiments are given as example only, and are not exhaustive of the scope of the technical solutions presented herein. Accordingly, the scope of protection is not limited to the preferred embodiments described in the specification, but is only limited by the claims that follow.

While the technical solutions presented herein have been depicted, described, and defined with reference to particular preferred embodiment(s), such references and examples of implementation in the foregoing specification do not imply any limitation on the invention. Various modifications and changes may be made thereto without departing from the scope of the technical solutions presented. The presented embodiments are given as example only, and are not exhaustive of the scope of the technical solutions presented herein. Accordingly, the scope of protection is not limited to the preferred embodiments described in the specification, but is only limited by the claims that follow.

The invention claimed is:

1. A hybrid TOF-PET/CT (Time-Of-Flight Positron Emission Tomography/Computed Tomography) tomograph comprising:
   a detection chamber having a longitudinal axis;
   gamma radiation detectors and X-ray detectors surrounding the detection chamber around a whole perimeter of the detection chamber; and
   a movable X-ray source;
   wherein the gamma radiation detectors are located closer to the longitudinal axis of the detection chamber than the X-ray detectors;
   and wherein the gamma radiation detectors comprise polymer scintillation strips made of a scintillation material having a density lower than the density of a scintillation material of the X-ray radiation detectors.

2. The hybrid tomograph according to claim 1, wherein the scintillation material of the polymer scintillation strips has a density below 1,2g/cm$^3$.

3. The hybrid tomograph according to claim 1, wherein the X-ray detectors have a density over 6g/cm$^3$.

4. The hybrid tomograph according to claim 1, wherein the polymer scintillation strips are penetrable for at least 60% of the X-rays.

5. The hybrid tomograph according to claim 1, wherein the polymer scintillation strips are arranged circumferentially such that the longest edges of the polymer scintillation strips are parallel to the longitudinal axis of the detection chamber.

6. The hybrid tomograph according to claim 5, wherein the polymer scintillation strips are adjacent to each other.

7. The hybrid tomograph according to claim 5, wherein the polymer scintillation strips are spaced with respect to their longest edges.

8. The hybrid tomograph according to claim 1, wherein X-ray detectors form a ring which is coaxial with the longitudinal axis of the detection chamber and which covers a TOF-PET detection layer.

9. The hybrid tomograph according to claim 1, wherein a layer of the X-ray detectors has a cross-section, perpendicular to the longitudinal axis of the detection chamber, in a form of an arc.

10. The hybrid tomograph according to claim 1, wherein an X-ray source is positioned between a layer of the gamma radiation detectors and a layer of the X-ray detectors.

11. The hybrid tomograph according to claim 10, wherein the X-ray source is positioned outside of a layer of the gamma radiation detectors.

12. The hybrid tomograph according to claim 10, wherein the X-ray source, during an X-ray emission, simultaneously rotates around and moves along the longitudinal axis of the detection chamber.

13. The hybrid tomograph according to claim 1, wherein the X-ray detectors change their position relative to the gamma radiation detectors.

14. The hybrid tomograph according to claim 1, wherein a collimated beam from the X-ray source does not pass through any of the polymer scintillation strips.

15. The hybrid tomograph according to claim 1, wherein a collimated beam from the X-ray source passes through two polymer scintillation strips.

16. The hybrid tomograph according to claim 1, wherein electronic devices connected to the gamma radiation detectors and to the X-ray detectors are located outside the detection chamber.

17. The hybrid tomograph according to claim 1, wherein the gamma radiation detectors and the X-ray detectors are connected to a common clock signal.

18. The hybrid tomograph according to claim 1, configured for simultaneous TOF-PET imaging and CT imaging.

19. The hybrid tomograph according to claim 1, configured for sequential TOF-PET imaging and CT imaging.

\* \* \* \* \*